(12) United States Patent
Bon

(10) Patent No.: US 6,855,137 B2
(45) Date of Patent: Feb. 15, 2005

(54) CATHETER SHAFT WITH COEXTRUDED STIFFENER

(75) Inventor: Edwin Bon, Canton, GA (US)

(73) Assignee: Visionary Biomedical, Inc., Roswell, GA (US)

( * ) Notice: Subject to any disclaimer, the term of this patent is extended or adjusted under 35 U.S.C. 154(b) by 177 days.

(21) Appl. No.: 10/093,757

(22) Filed: Mar. 7, 2002

(65) Prior Publication Data

US 2003/0171736 A1 Sep. 11, 2003

(51) Int. Cl.⁷ ............... A61M 25/00; A61M 25/01; A61M 25/02; A61M 25/04; A61M 25/06; A61M 25/08; A61M 25/082; A61M 25/085; A61M 25/088; A61M 25/09; A61M 25/095; A61M 25/098; A61M 5/178; C04B 35/64

(52) U.S. Cl. ............... 604/525; 604/528; 604/164.13; 264/634

(58) Field of Search ............... 604/510, 95.04, 604/164.13, 524, 525, 528; 600/434; 264/514, 515, 516, 541, 171.26–171.29, 172.1–172.15, 173.11–173.17, 177.1

(56) References Cited

U.S. PATENT DOCUMENTS

| | | | |
|---|---|---|---|
| 4,250,072 A | * | 2/1981 | Flynn ............... 524/288 |
| 5,226,899 A | | 7/1993 | Lee et al. |
| 5,453,099 A | | 9/1995 | Lee et al. |
| 5,542,937 A | | 8/1996 | Chee et al. |
| 5,797,882 A | | 8/1998 | Purdy et al. |
| 5,902,287 A | | 5/1999 | Martin |
| 5,976,120 A | * | 11/1999 | Chow et al. ............... 604/525 |
| 6,004,310 A | * | 12/1999 | Bardsley et al. ............ 604/524 |
| 6,027,477 A | | 2/2000 | Kastenhofer |
| 6,030,369 A | | 2/2000 | Engelson et al. |
| 6,325,790 B1 | | 12/2001 | Trotta |
| 6,530,897 B2 | * | 3/2003 | Nardeo ............... 604/95.04 |

OTHER PUBLICATIONS

Plastics Technology Online Article "Medical Tubing Coextrusion Brings a New Level of Care" by Jan H. Schut, 6 pgs.

\* cited by examiner

*Primary Examiner*—Nicholas D. Lucchesi
*Assistant Examiner*—Catherine S. Williams
(74) *Attorney, Agent, or Firm*—Gardner Groff, P.C.

(57) ABSTRACT

A steerable catheter having a shaft with one or more internal stiffeners coextruded within the shaft along a portion of its length. The internal stiffeners have a higher or lower hardness than the body of the catheter shaft. The overall stiffness of the shaft varies along its length for improved steerability.

13 Claims, 2 Drawing Sheets

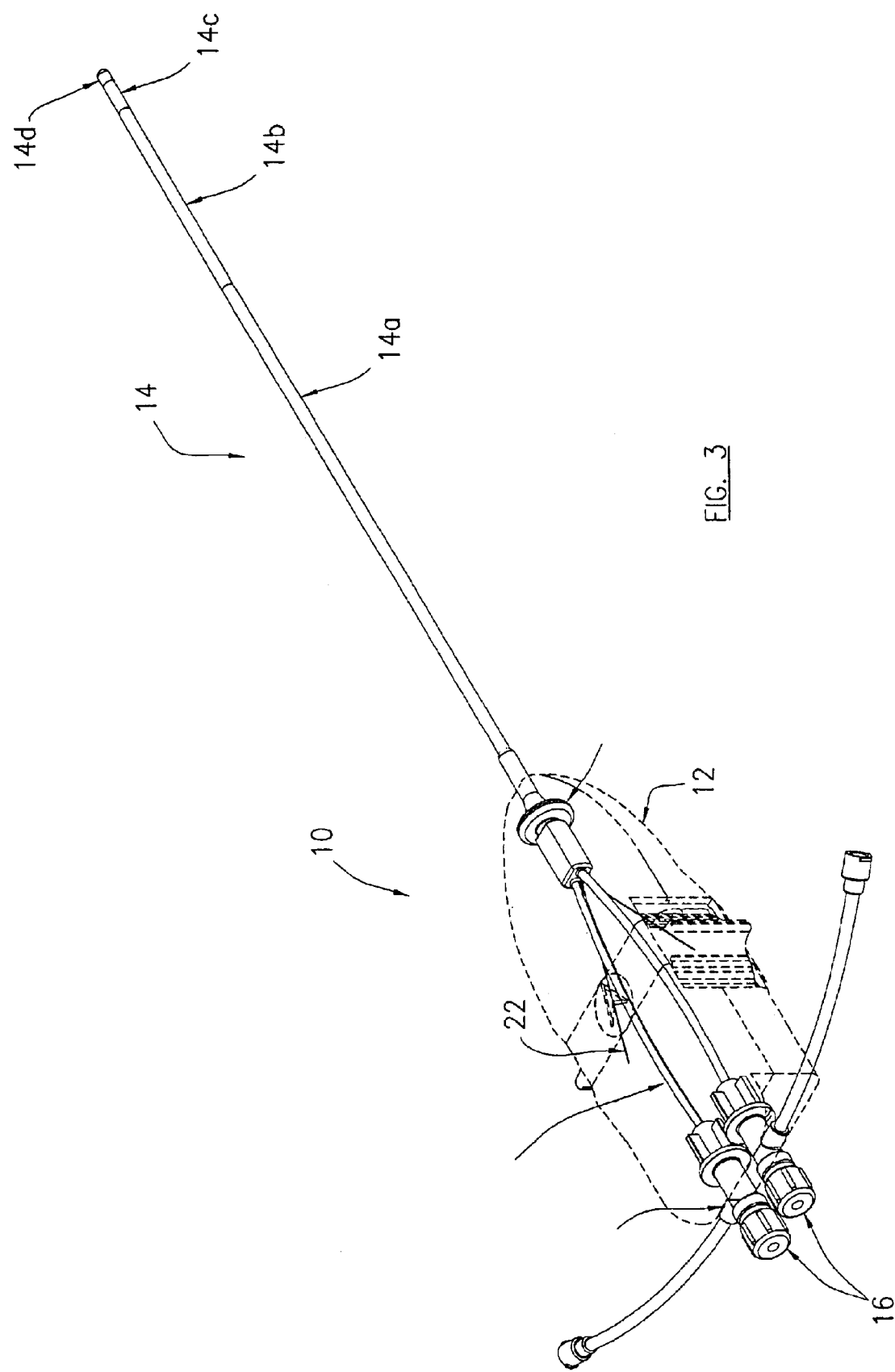

CATHETER SHAFT WITH COEXTRUDED STIFFENER

BACKGROUND OF THE INVENTION

1. Field of the Invention

The present invention relates generally to remote access devices, and more particularly to a steerable catheter having one or more stiffeners coextruded into the catheter shaft.

2. Description of Related Art

Modern medical practitioners frequently gain access to internal regions of a human or animal patient's body through the use of medical catheters in a variety of medical procedures. For example, medical catheters may be used to access internal body regions with a fiberoptic scope, light bundles, surgical instruments, medications, and/or other substances and devices, for a variety of diagnosis, treatment and/or material delivery purposes. These minimally invasive catheter access techniques can significantly reduce or eliminate the need for more invasive procedures.

Steerable catheters have been developed to provide improved access to remote sites such as internal body tissue. These catheters typically include a flexible catheter shaft and steering wires or other means for controlling the flexure of the catheter shaft. Steerable catheters find application in the observation and treatment of tissue in and around the joints in arthroscopic procedures, in and around the abdominal cavity in laparoscopic procedures, in spinal epiduroscopy, in the cardio-pulmonary and circulatory systems, and in other endoscopic procedures. Steerable catheters are also used for remote visualization and access in non-medical applications such as in the inspection and repair of internal engine components and other devices and structures.

A commonly encountered problem in the design of steerable catheters is the provision of acceptable flexibility of the catheter shaft, particularly near the shaft tip, while still maintaining adequate overall shaft stiffness for pushing through tissue openings and other access pathways. Difficulties are also encountered in providing a desired degree of stiffness to a catheter shaft formed from the relatively softer shaft materials that are often preferred for their trauma minimization qualities. Also, in most instances it would be desirable to provide a catheter shaft with a more "in-plane" steering bias for improved steering control, rather than a shaft that tends to twist or "pig-tail" out of the intended steering plane when steered. Another problem suffered by some previously existing catheter shafts is "socking", wherein the shaft material crumples along the shaft's longitudinal axis when tension is applied to the steering wires, rather than bending along a smooth arcuate path.

Previously known methods of forming catheter shafts have also been found to have certain drawbacks. For example, some catheter shafts incorporate wire reinforcements encapsulated into their wall material or concentrically coextruded layers, which result in manufacturing difficulties and add considerably to the shaft's expense. In addition, the inclusion of wire within a catheter shaft may interfere with the guidance and placement of the catheter under flouroscopic observation, or may adversely impact regulatory approvals. Also, the material dissimilarities between the metal wire and the polymeric catheter shaft may result in slippage therebetween, possibly producing unpredictable steering characteristics. Welding shaft segments of differing durometer hardness together to form a catheter shaft also requires considerable effort and expense in ensuring proper alignment and connection between the segments.

Thus, it has been found that needs exist for an improved steerable catheter shaft and to related production methods. It is to these and other needs that the present invention is primarily directed.

SUMMARY OF THE INVENTION

Briefly described, in its preferred embodiments, the present invention provides a steerable catheter shaft having one or more internal stiffeners coextruded or otherwise formed into the shaft material along a selected portion of the length of the shaft. The stiffener(s) assist in maintaining the overall stiffness of the shaft, and resist socking. Because the stiffener(s) is/are embedded within the body of the shaft, the shaft's exterior can be formed of a softer, atraumatic material. Eccentric placement of the stiffener(s) biases the shaft to steer in an in-plane manner. The configuration of the stiffener(s)—including the size, shape, number and location of the stiffener(s) within the shaft's cross-section and/or along the shaft's length—can be selectively controlled to vary the flexibility and steerability characteristics of the shaft. One or more instrument lumens preferably extend through the catheter shaft for instrument access and/or passage of fluids, medication and the like. One or more steering wires preferably pass through at least a portion of the catheter shaft to effect steering of the shaft. Optionally, the lumen(s) and/or the steering wire(s) pass through the stiffener(s) within the catheter shaft.

In one embodiment, the present invention is a catheter shaft. The catheter shaft preferably includes a shaft body formed of a polymeric material having a first hardness, and the shaft body has a first end and a second end and defines a length therebetween. The shaft preferably also includes at least one stiffener embedded within the shaft body along at least a portion of the length of the shaft body. Each stiffener is preferably formed of a polymeric material having a second hardness different than the first hardness.

In another embodiment, the present invention is a steerable catheter. The catheter preferably includes an elongate catheter shaft having a first end and a second end, and defines a length between the first and second ends. The catheter preferably also includes at least one internal stiffener embedded within the catheter shaft, and at least one steering wire extending through at least a portion of the length of the catheter shaft.

Another embodiment of the present invention is a steerable catheter. The catheter preferably includes a handle having at least one steering actuator. The catheter preferably also includes a catheter shaft having a proximal end connected to the handle, a distal end opposite the proximal end, and defining a length between the proximal and distal ends. The catheter shaft preferably includes at least one instrument lumen and at least one steering wire lumen. The catheter preferably also includes at least one stiffener coextruded within the catheter shaft, and at least one steering wire extending through the at least one steering wire lumen of the catheter shaft and being connected to the steering actuator.

In another embodiment, the present invention is a method of forming a catheter shaft. The method preferably includes extruding a first polymeric material to form a shaft body, the first polymeric material having a first hardness; and coextruding a second polymeric material to form at least one stiffener within the shaft body, the second polymeric material having a second hardness different from the first hardness.

These and other features and advantages of preferred forms of the present invention are described herein with reference to the drawing figures.

BRIEF DESCRIPTION OF THE DRAWING FIGURES

FIG. 3 shows a perspective view of a catheter according to an embodiment of the present invention.

DETAILED DESCRIPTION

Figure 1:
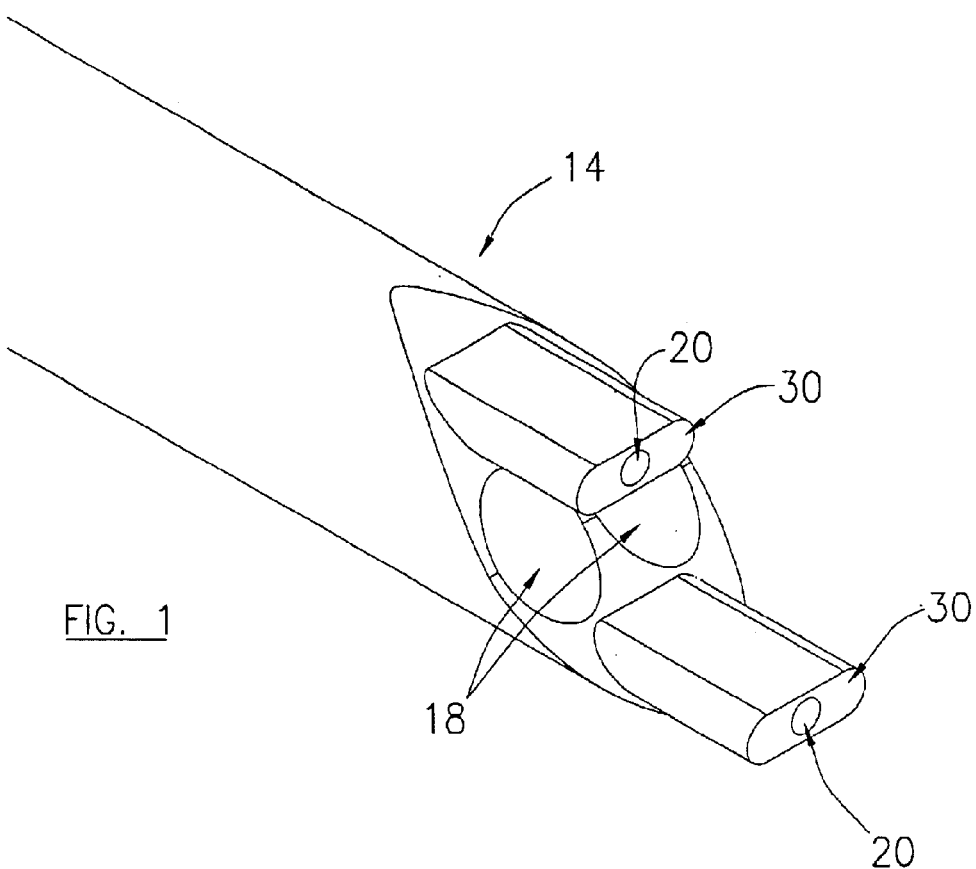
FIG. 1 shows a perspective view of a shaft portion of a steerable catheter in partial cutaway, according to one embodiment of the present invention.

Referring now to the drawing figures, in which like reference numbers refer to like parts throughout, preferred forms of the present invention will now be described by way of example embodiments. It is to be understood that the embodiments described and depicted herein are only selected examples of the many and various forms that the present invention may take, and that these examples are not intended to be exhaustive or limiting of the claimed invention. Also, as used in the specification including the appended claims, the singular forms "a," "an," and "the" include the plural unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

As seen best with reference to FIGS. 1 and 3, a catheter 10 according to one example embodiment of the present invention generally comprises a handle 12 and a shaft 14 extending from the handle. The handle 12 preferably comprises one or more steering actuator(s), such as a steering dial, one or more steering buttons, one or more levers or wire pulls, or the like. The catheter 10 optionally further comprises one or more inlet housings 16 in communication with lumens extending through the shaft 14. U.S. Pat. No. 6,030,360, which is hereby incorporated herein by reference, shows an example of a steerable catheter with a dial-actuated steering mechanism.

In example embodiments, the catheter shaft 14 of the present invention has a proximal end connected to the handle 12 and a distal free end or tip opposite the proximal end, and defines a shaft length between the proximal and distal ends. The body of the shaft 14 is preferably formed of a flexible and biocompatible polymeric material, for example a 5533 Pebax® polyether block amide. The shaft 14 optionally is marked, compounded, coated, or otherwise provided with one or more additive materials, colorants, or markings such as barium sulfate and/or titanium oxide to permit flouroscopic observation and positioning of the shaft. In one example embodiment, the shaft 14 has an outside diameter of about 0.100", and a length of about 12". Of course, shafts of larger or smaller diameter and length may be desirable for particular applications, and are within the scope of the invention. Although the embodiment of the shaft 14 depicted in the figures has a generally round cross-sectional profile (see FIG. 2), shafts of flat, oval, triangular, square, rectangular, polygonal or other cross-sectional profiles are also within the scope of the invention.

One or more instrument lumens 18 preferably extend through at least a portion of the length of the shaft 14. The instrument lumens 18 are preferably sized and/or shaped to accommodate passage of various medical instruments, light guides, fiberscopes and/or other items, and/or to communicate fluids, medication and/or other materials for the treatment, aspiration, dilation, distension, insufflation, etc. of targeted body tissue. In the depicted embodiment, the catheter shaft 14 defines two instrument lumens 18, each extending through substantially the entire length of the shaft 14, and each having a central axis lying on a first plane X extending through the shaft. In an example embodiment of the invention, each of the instrument lumens 18 have an inside diameter of about 0.042" and are separated by a web thickness of at least 0.006". Of course, larger or smaller diameter instrument lumens 18 and lumens of different sizes and/or shapes are also within the scope of the invention. The interior surface of the instrument lumens may be coextruded or coated with a low friction material, a chemical-resistant material, and/or other material(s) having qualities desirable for particular applications.

One or more steering wire lumens 20 preferably also extend through at least a portion of the length of the shaft 14. One or more steering wires 22 preferably extend through the steering wire lumens 20 and are attached to the steering actuator of the handle 12 to permit a user to selectively steer or flex at least a portion of the shaft 14 in a desired direction and to a desired degree of flexure. In the depicted embodiment, the catheter shaft 14 defines two steering wire lumens 20. Each of the steering wire lumens 20 has a central axis lying on a second plane Y extending through the shaft, the second plane Y being oriented generally perpendicular to the first plane X In an example embodiment of the invention, each of the steering wire lumens 20 have an inside diameter of about 0.014". Of course, larger or smaller diameter instrument lumens 18 and lumens of shapes other than round are also within the scope of the invention.

Figure 2:
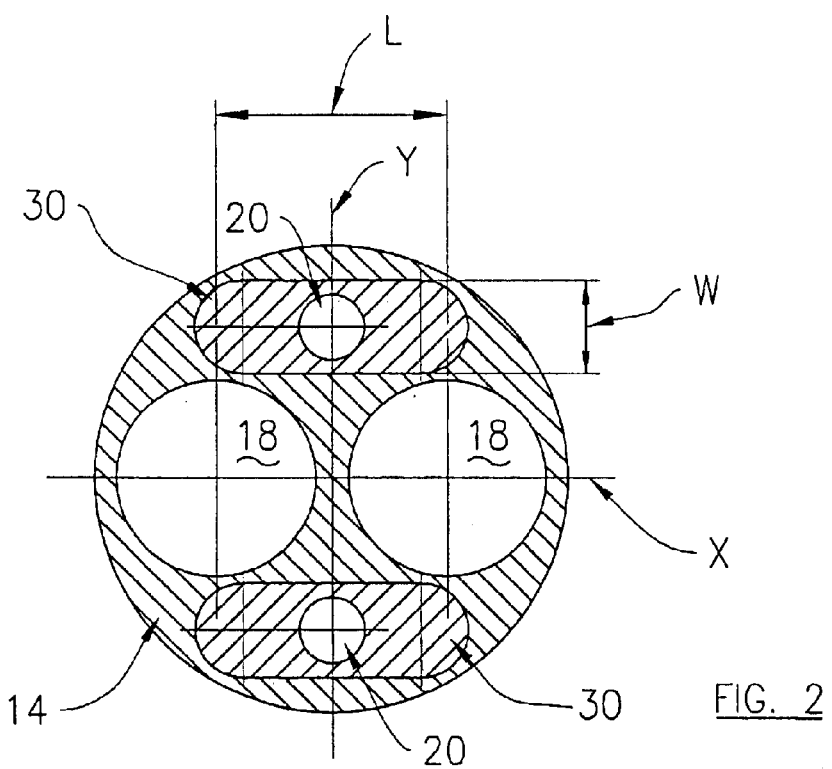
FIG. 2 shows a cross-sectional view of the shaft portion of a steerable catheter shown in FIG. 1.

One or more stiffeners 30 are preferably embedded within the body of the catheter shaft 14, as shown for example in FIGS. 1 and 2. The stiffener(s) 30 are preferably formed of a material having a different hardness than the material of the body of the shaft 14, whereby the stiffeners alter the steering characteristics of the shaft. The stiffener(s) 30 are preferably formed of a polymeric material, such as for example Pellethane® 2363-75D thermoplastic polyurethane elastomer. In preferred form, the stiffener(s) 30 are embedded within the body of the shaft 14 by coextrusion, and are entirely surrounded on their sides and ends by the shaft body material. In this manner, the stiffeners 30 do not substantially alter the surface characteristics of the exterior of the shaft 14 or of the interior of the lumens. For example, the atraumatic qualities of a relatively soft material forming the body of the shaft 14 will not be adversely affected to any significant degree by an encapsulated stiffener 30 of a relatively harder material. Also, encapsulation of the stiffener(s) 30 within the material of the body of the shaft 14 prevents the stiffener(s) from slipping within the shaft, even in the absence of a material bond between the shaft and the stiffener(s).

The presence of a "stiffener" can increase or decrease the stiffness of the portion of the shaft that the stiffener is contained within. For example, the material of the stiffener 30 can be harder than the catheter body material, such that a portion of the shaft comprising the stiffener is more stiff (i.e., less steerable) than a portion of the shaft from which the stiffener is omitted (i.e., a "positive" stiffener); or alternatively the material of the stiffener 30 can be softer than the catheter body material, such that the portion of the shaft comprising the stiffener is less stiff (i.e., more steerable) than the portion of the shaft from which the stiffener is omitted (i.e., a "negative" stiffener).

The stiffener(s) 30 extend through at least a portion of the length of the shaft 14, and preferably extend generally parallel to the central longitudinal axis (the intersection of plane X and plane Y) of the shaft body. Most preferably, the stiffeners 30 extend only partially through the length of the shaft 14, and are omitted from the remainder of the length of the shaft. Segments of the shaft from which stiffeners are omitted preferably comprise a homogenous cross section entirely formed of the shaft body material. For example, and with particular reference now to FIG. 3, one or more positive stiffeners 30 are preferably embedded within a proximal segment 14a of the shaft 14, and stiffeners are omitted from a distal segment 14b of the shaft. In this manner, actuation of the steering mechanism results in flexure of the distal segment 14b, whereas the proximal segment 14a remains generally straight or flexes to a lesser degree than the distal segment. In an alternate embodiment, one or more negative stiffeners are embedded within the distal segment 14b of the shaft, and stiffeners are omitted from the proximal segment 14a, thereby also resulting in a greater degree of flexure of the distal segment upon steering. In still another embodiment, one or more stiffeners 30 extend through substantially the entire length of the shaft 14, each stiffener comprising a first stiffener section formed of a first material and a second stiffener section formed of a second material having a hardness different than that of the first material. This embodiment can, for example, be formed by sequentially coextruding the first stiffener section of a relatively harder material into the proximal shaft segment 14a, and the second stiffener section of a relatively softer material into the distal shaft segment 14b. Of course, depending upon the intended application, it may be desirable to provide greater flexibility to proximal and/or medial shaft segments than to distal shaft segments, and/or to provide two or more segments of increased flexibility spaced at different locations along the shaft.

One or more additional shaft segments, such as tip segment 14c and cover segment 14d are optionally provided, and may or may not include stiffeners 30. These additional segments, for example, can be sequentially coextruded with or adhered or welded onto the remainder of the shaft 14, and can be formed of the same or different materials as the remainder of the shaft, as to provide an atraumatic tip, improved flouroscopic visibility of the tip, resistance to steering wire pull-through, and/or other desired shaft characteristics.

One or more of the stiffeners 30 is preferably positioned eccentrically within the cross-sectional profile of the body of the catheter shaft 14, with its center located a distance away from the central longitudinal axis (the intersection of plane X and plane Y) of the shaft body. This off-center location of the stiffener(s) helps bias the shaft 14 to flex in an in-plane manner, rather than twisting or "pig-tailing" when steered. Additionally or alternatively, one or more of the stiffeners 30 are asymmetric, having a first dimension in one direction that is greater than a second dimension in another direction. For example, in the depicted embodiment, and with particular reference now to FIG. 2, each of the two stiffeners 30 has a central axis lying on plane Y, and has a first dimension or length L in a direction parallel to plane X that is greater than a second dimension or width W in a direction parallel to plane Y. More preferably the first dimension L is at least twice the second dimension W. The asymmetric nature of the stiffeners also helps bias the shaft 14 to steer in an in-plane manner. For example, the shaft 14 will generally tend to flex in the direction of the minor (i.e., smaller) dimension of the stiffeners. In other words, in the depicted embodiment, the shaft 14 will be biased to flex in plane Y. In addition to the size, shape, number and location of the stiffeners 30, the steering bias of the shaft 14 can be selectively varied by appropriate selection of the size, shape, number and location of the lumens 18, 20 and of the steering wires 22. For example, in the depicted embodiment, the two steering wire lumens 20 extend through the central axes of the stiffeners 30, which lie on plane Y, further biasing the shaft 14 to flex in plane Y.

The stiffeners 30 and the body of the shaft 14 are preferably formed of dissimilar materials that are not entirely compatible with one another, in that the materials do not blend freely or molecularly integrate with one another during coextrusion. For example, a shaft body 14 of a polyether block amide material and a stiffener 30 of thermoplastic polyurethane elastomer have been found to resist significant blending during coextrusion. In this manner, the material of the stiffeners 30 remains generally heterogenous from the material of the shaft body 14, and the intended geometry and location of the stiffeners within the shaft body is maintained. Preferably, however, a slight degree of melting together of the materials occurs at the transition between the stiffeners and the shaft body to create a material bond and prevent slippage therebetween, ensuring that the shaft and stiffeners flex as a unitary body. Alternatively, the materials of the stiffeners and the shaft body are compatible and some degree of intermixing occurs during coextrusion; but the stiffeners nevertheless remain generally in the intended location and geometry, albeit with some spreading at the material transition.

The present invention also includes methods of forming a steerable catheter as disclosed herein. Example embodiments of fabrication methods according to the present invention include extruding a first polymeric material to form a shaft body, the first polymeric material having a first hardness; and coextruding a second polymeric material to form at least one stiffener within the shaft body, the second polymeric material having a second hardness different from the first hardness. In one embodiment, the first polymeric material has a higher hardness than the second polymeric material. In an alternate embodiment, the second polymeric material has a higher hardness than the first polymeric material. The at least one stiffener is preferably coextruded within only a portion of the length of the shaft body, to form shaft segments of differing degrees of steerability. Preferably, at least one of the stiffeners is coextruded into the shaft body at a distance from a central longitudinal axis of the shaft body. Additionally or alternatively, at least one of the stiffeners is coextruded to have a cross sectional length and a cross sectional width, the cross sectional length being greater than the cross sectional width. In alternate embodiments, at least one of the stiffeners is sequentially coextruded from the second polymeric material and a third polymeric material, the third polymeric material having a third hardness different from the first and second hardnesses. An entire catheter shaft can be formed as a single extrusion by sequential coextrusion of the respective segments of the entire shaft, including segments having one or more stiffeners embedded therein and segments without stiffeners. Alternatively, segments having one or more stiffeners are coextruded separately from segments without stiffeners, the segments are cut to the intended lengths, and the segments are then aligned and welded or otherwise attached to one another to form the catheter shaft.

While the invention has been described in its preferred forms, it will be readily apparent to those of ordinary skill in the art that many additions, modifications and deletions can be made thereto without departing from the spirit and scope of the invention.

What is claimed is:

1. A steerable catheter comprising:
   a handle comprising at least one steering actuator;
   a catheter shaft having a proximal end connected to the handle, a distal end opposite the proximal end, and defining a length between said proximal and distal ends, said catheter shaft comprising at least steering wire lumen;
   at least one steering wire extending through said at least one steering wire lumen of the catheter shaft and connected to said steering actuator;
   two instrument lumens extending along the length of the catheter shaft, each of said two instrument lumens having a central axis lying on a first plane being extending through said catheter shaft; and
   two stiffeners coextruded within said catheter shaft and extending along at least a portion of the length of the catheter shaft, each of said two stiffeners having a central axis lying on a second plane extending through said catheter shaft, the second plane being generally perpendicular to the first plane.

2. The steerable catheter of claim 1, wherein a steering wire lumen extends through each stiffener.

3. The steerable catheter of claim 1, wherein each stiffener has a first dimension in a direction parallel to said first plans, and a second dimension in a direction parallel to said second plane, and wherein said first dimension is greater than said second dimension.

4. The steerable catheter of claim 3, wherein said first dimension is at least twice said second dimension.

5. The steerable catheter of claim 1, wherein the stiffeners have a higher hardness than the catheter shaft.

6. The steerable catheter of claim 1, wherein the catheter shaft has a higher hardness than the stiffeners.

7. The steerable catheter of claim 1, wherein the stiffeners extend through less than the entire length of the catheter shaft.

8. A method of forming a catheter shaft, said method comprising:
   extruding a first polymeric material to form a shaft body, the first polymeric material having a first hardness;
   coextruding a second polymeric material to form two stiffeners within the shaft body, the second polymeric material having a second hardness different from the first hardness;
   wherein at least one of said stiffeners is sequentially coextruded from said second polymeric material and a third polymeric material, said third polymeric material having a third hardness different from the first and second hardnesses; and
   wherein the shaft body has at least one steering wire extending through at least one steering wire lumen of the shaft body and two instrument lumens extending along the length of the shaft body, each of said two instruments lumens having a central axis lying on a first plane extending through said shaft body, and said two stiffeners extending along at least a portion of the length of the shaft body, each of said two stiffeners having a central axis lying on a second plane extending through said shaft body, the second plane being generally perpendicular to the first plane.

9. The method of claim 8, wherein the first polymeric material has a higher hardness than the second polymeric material.

10. The method of claim 8, wherein the second polymeric material has a higher hardness than the first polymeric material.

11. The method of claim 8, wherein the at least one stiffener is coextruded within only a portion of the length the shaft body.

12. The method of claim 8, wherein the at least one stiffener is coextruded into the shaft body at a distance from a central longitudinal axis of the shaft body.

13. The method of claim 8, wherein the at least one stiffener is coextruded to have a cross sectional length and a cross sectional width, said cross sectional length being greater than said cross sectional width.

* * * * *